United States Patent [19]

Takesue et al.

[11] Patent Number: 5,673,341
[45] Date of Patent: Sep. 30, 1997

[54] INTRA-LIQUID OPTICAL MEASURING SENSOR AND CONTAMINATION PREVENTING METHOD

[75] Inventors: Hiroto Takesue; Tsugio Shimono, both of Tokyo, Japan

[73] Assignee: NEC Corporation, Japan

[21] Appl. No.: 584,777

[22] Filed: Jan. 11, 1996

[30] Foreign Application Priority Data

Jan. 13, 1995 [JP] Japan .................................. 7-003921
Aug. 25, 1995 [JP] Japan .................................. 7-217331

[51] Int. Cl.$^6$ ................................................ G02B 6/00
[52] U.S. Cl. ................................ 385/12; 250/227.11
[58] Field of Search ........................... 385/12, 123, 125, 385/117; 356/352, 345, 128, 136; 250/227.11

[56] References Cited

U.S. PATENT DOCUMENTS

| | | | |
|---|---|---|---|
| 4,201,446 | 5/1980 | Geddes et al. | 385/125 |
| 4,832,444 | 5/1989 | Takahashi et al. | 385/117 |
| 4,927,231 | 5/1990 | Levatter | 385/125 X |
| 5,165,773 | 11/1992 | Nath | 385/125 |
| 5,381,231 | 1/1995 | Tu | 356/352 |
| 5,493,629 | 2/1996 | Stange | 385/12 X |

FOREIGN PATENT DOCUMENTS

| | | |
|---|---|---|
| 58-103345 | 7/1983 | Japan . |
| 61-143587 | 7/1986 | Japan . |
| 62-176217 | 11/1987 | Japan . |
| 2-43673 | 3/1990 | Japan . |

*Primary Examiner*—Akm E. Ullah
*Attorney, Agent, or Firm*—Hayes, Soloway, Hennessey, Grossman & Hage, P.C.

[57] ABSTRACT

An intra-liquid optical measuring sensor is provided having an optical fiber including a cladding in the form of a hollow tube, and a core. The core includes both a solid portion, and a liquid portion at an end of the core, which latter portion serves as the sensing portion of the fiber. The liquid portion has a light transmitting liquid substance therein.

14 Claims, 4 Drawing Sheets

INTRA-LIQUID OPTICAL MEASURING SENSOR AND CONTAMINATION PREVENTING METHOD

BACKGROUND OF THE INVENTION

1. Field of the Invention

This invention relates to an intra-liquid optical measuring sensor which is used in liquid and a contamination preventing method for the intra-liquid optical measuring sensor, and more particularly to an intra-liquid optical measuring sensor which is high in resistance to pollution damage and can be used continuously for a long period of time and a contamination preventing method for the intra-liquid optical measuring sensor.

2. Description of the Related Art

One measuring technique which makes use of an optical fiber is used widely for qualitative and quantitative evaluations such as illumination characteristics, dissolved substances and species of organisms in liquid such as in water or in the sea. As a measuring method, normally an optical fiber is used as a sensor, and an end of the core (waveguide) of the optical fiber is contacted with liquid of an object of measurement such that optical information inputted thereto from the object liquid is transmitted to a measuring instrument using the optical fiber as a conductor.

For such measurement, continuous measurement for a long period of time, spanning over several months to several years has been demanded for a long time. However, continuous measurement cannot actually be readily realized due to the significant obstacle caused by organisms or contaminants deposited onto the optical fiber or by pollution of the optical fiber caused by such deposited substances.

Conventionally, as a contamination preventing method for underwater measurement, countermeasures of coating marine structures with anti-fouling paint containing various organic tin compounds, cuprous oxide or a like compound or removing the fouling substances using a physical technique have been used. Also suppression of deposition of biological fouling materials by using a hypochlorous acid which is produced by electrolysis of sea water has been used (Japanese Patent Laid-Open Application No. Showa 61-143587, Japanese Utility Model Laid-Open Application No. Showa 58-103345).

Further, an apparatus for preventing deposition of organisms onto a measuring instrument or a like element installed in sea water that makes use of fresh water has been reported (Japanese Utility Model Laid-Open Application No. Heisei 2-43673, Japanese Utility Model Laid-Open Application No. Showa 62-176217).

Most of the prior art contamination preventing coating materials described above which have been proved to be effective are considered to have a bad influence on the environment when they are used, and it is difficult to use them due to the recent growing tendency for environmental conservation. Recently, silicone resin coating materials have been and are being investigated to obtain a pollution-free contamination preventing coating material (Maritime organism anti-pollution manual, the Society of Electrochemistry, Gihodo). Further, even if some of the prior art materials can be used, they cannot be applied directly to a light inputting/outputting surface of an optical fiber sensor because of the need for transmission of light therethrough.

On the other hand, the physical (mechanical) technique is inferior in reliability in the apparatus for removing a deposited substance itself because the apparatus is within liquid and hence in an environment in which maintenance thereof is difficult.

The technique of making use of an oxidizing capacity of hypochlorous acid produced by electrolysis is effective for preventing contamination by organisms themselves. However, for dead bodies of organisms, floating substances in the form of sludge and like substances, the technique is not effective to prevent deposition or to remove deposited substances.

Some conventional organism deposition preventing apparatuses which make use of fresh water have, for example, a function or a construction for jetting fresh water onto a measuring instrument and so forth or covering a measuring instrument with a cover so as to cause fresh water to stay therein. However, where fresh water is jetted or caused to stay intermittently, the jetting or retention time must be set. However, since the amount of deposited organisms in sea water depends much upon the depth in the water, the environment, the season and so forth of a region of the sea in which the organism deposition preventing apparatus is installed, the organism deposition preventing apparatus has the problem that setting of the jetting or retention time is very delicate and is difficult to optimize.

Further, with the conventional retention method wherein fresh water is supplied intermittently, since the fresh water is replaced with sea water by a flow of sea water caused by an ocean current or the like and is lost readily, in order to suppress deposition of organisms effectively, a large amount of fresh water must be supplied. However, upon measurement of a physical amount or a chemical amount in the sea, since the environment of the measurement object region is varied by the presence of a large amount of fresh water or a cover, either the measurement in the time period in which jetting proceeds or fresh water is retained is impossible or the accuracy in measurement is very low.

Further, since the jetting apparatus itself is in sea water, also the reliability of the apparatus is low due deposition of organisms and so forth.

SUMMARY OF THE INVENTION

It is an object of the present invention to provide an intra-liquid optical measuring sensor which has a function of suppressing depositions of organisms onto a light inputting/outputting surface of an optical fiber sensor used in liquid and another function of removing deposited substances so that it solves the problem of contamination of the sensor and keeps a high degree of reliability even when it is used continuously for a long period of time and a contamination preventing method for the intra-liquid optical measuring sensor.

According to the present invention, an intra-liquid optical measuring sensor and a contamination preventing method are constructed such that a portion of the intra-liquid optical measuring sensor making use of an optical fiber which contacts with liquid which is an object of measurement of the optical fiber is a liquid substance having a light transmitting property.

The intra-liquid optical measuring sensor may comprise a supply apparatus for supplying the liquid substance to the liquid substance portion of the core of the optical fiber or may comprise a recovery apparatus for recovering a portion of the liquid substance which overflows from the optical fiber.

Further, a capillary pipe having an inner diameter equal to or greater than an outer diameter of the core of the optical fiber and within a range within which a liquid substance in the inside of the capillary pipe can be held by a surface tension of an inner face of the capillary pipe and a pressure by liquid of an object of measurement may be attached to an end of the optical fiber such that the inner diameter portion of the capillary pipe is disposed on an extension line of the core while the inner diameter portion is filled with a liquid substance having a light transmitting property. The intra-liquid optical measuring sensor may further comprise a supply apparatus for supplying the liquid substance to the liquid substance portion of the core in the capillary pipe or may further comprise a recovery apparatus for recovering a portion of the liquid substance which overflows from within the capillary pipe.

The intra-liquid optical measuring sensor may comprise a monitor for measuring an amount of reflected light produced at an end surface of the core of the liquid substance, and a control apparatus for controlling an amount of the liquid substance to be supplied in accordance with a result of the measurement of the monitor.

Silicone oil or water may be used as the liquid substance of the core.

A contamination preventing method for an intra-liquid optical measuring sensor formed from an optical fiber is accomplished such that a contacting face of a core of the optical fiber for contacting with a liquid of an object of measurement is formed from a liquid substance to which contaminant substances are less likely to be deposited.

The liquid substance may be supplemented from the outside to renew the liquid substance at the contacting portion of the liquid substance with the liquid of the object of measurement. Deposition of organisms occurs with a structure in liquid which has a certain hardness. According to the method of the present invention, since the object of deposition is a liquid substance, deposition is suppressed due to the effects of the smoothness of the surface, the fluidity and so forth. Further, even if deposition occurs, due to the increase in weight as the deposit grows, the deposit is exfoliated and removed together with part of the liquid substance. where a liquid substance having a high water repellency and a high hydrophobic property such as silicone oil is used, the amount of organisms which may be deposited is further reduced. Since maritime organisms cannot live in fresh water, where the intra-liquid optical measuring sensor is used in sea water, contamination by maritime organisms can be reduced by using fresh water as the liquid substance.

Further, with the method wherein the liquid substance is supplied to the liquid substance of the core from the outside, the liquid substance which contacts with the liquid of the object of measurement is renewed together with the contaminant substances.

Where the recovery apparatus for the liquid substance is provided, scattering of the overflowing liquid substance and contaminant substances into the liquid of the object of measurement can be prevented.

Further, with the intra-liquid optical measuring sensor which comprises the monitor for measuring the amount of reflected light produced at an end surface of the core of the liquid substance and the control apparatus for controlling the amount of the liquid substance to be supplied in accordance with a result of the measurement of the monitor, the shape of the end surface of the core can be controlled so as to a desirable shape.

The above and other objects, features, and advantages of the present invention will become apparent from the following description based on the accompanying drawings which illustrate an example of a preferred embodiment of the present invention.

BRIEF DESCRIPTION OF THE DRAWINGS

FIGS. 7(a) to 7(c) are partial sectional views showing different shapes of a light inputting/outputting surface of a liquid core of a seventh embodiment of the present invention and relationships between incident light and reflected light, and wherein FIG. 7(a) shows an end face of the liquid core curved toward the inside of the cladding, FIG. 7(b) shows a flat end face of the liquid core, and FIG. 7(c) shows an end surface of the liquid core curved toward the outside of the cladding.

DETAILED DESCRIPTION OF THE PREFERRED EMBODIMENTS

Preferred embodiments of the present invention are described below with reference to the drawings.

Figure 1:
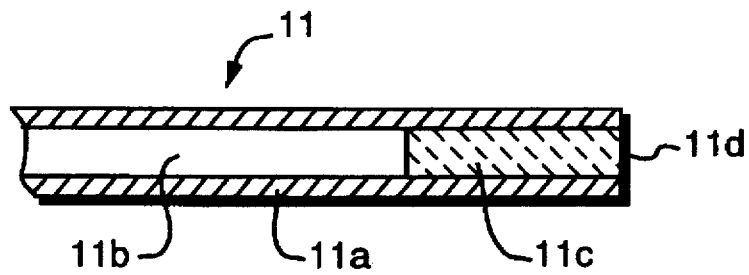
FIG. 1 is a partial sectional view of an intra-liquid optical measuring of the present invention.

FIG. 1 is a partial sectional view of an intra-liquid optical measuring sensor of a first embodiment of the present invention. Optical fiber 11 employed for the sensor is formed normally from cladding 11a in the form of a hollow tube, and core (solid) 11b in the form of a wire having clad ha fitted around an outer face thereof. In the sensor of the present invention, however, core (solid) lib at an end portion of optical fiber 11 which serves as a sensing portion is replaced by core (liquid) 11c of a liquid substance having a light transmitting property.

When the present sensor is immersed in liquid of an object of measurement, a liquid-liquid interface is formed between light inputting/outputting surface lid of the core and the liquid of the object of measurement. Since the inner diameter of cladding 11a of optical fibers used for the object of the type described is usually approximately several hundreds of microns to several mm, the liquid filling cladding 11a can be held in the inside of cladding 11a readily by capillary phenomenon.

Figure 2:
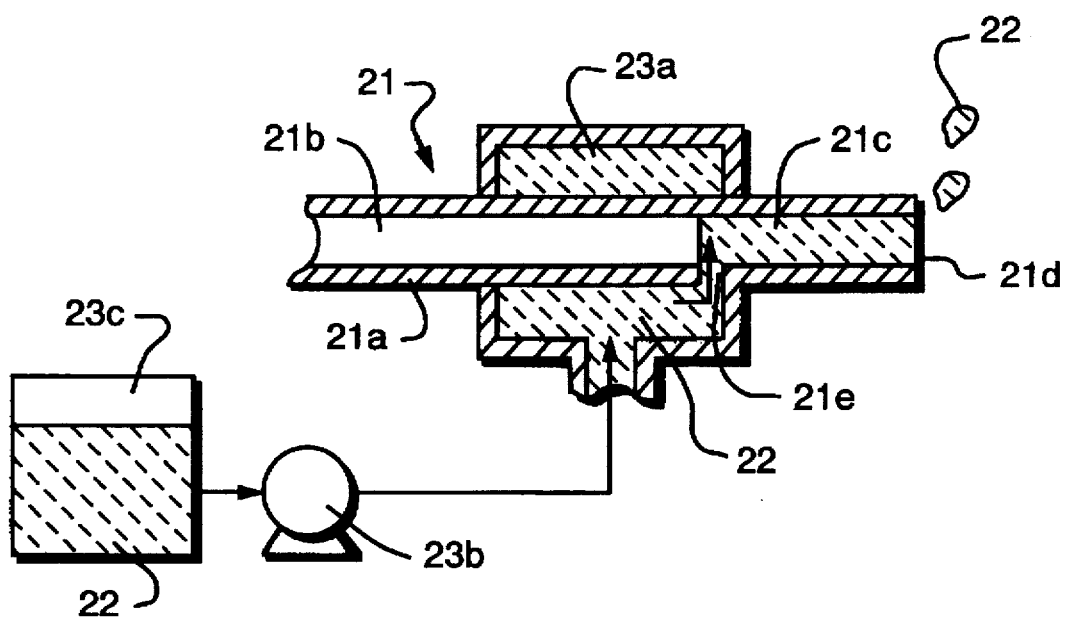
FIG. 2 is a partial liquid optical measuring of the present invention.

FIG. 2 is a partial sectional view of an intra-liquid optical measuring sensor of a second embodiment of the present invention. A supplying apparatus for liquid substance 22 is formed from supply chamber 23a, supply pump 23b and reservoir 23c. Supply port 21e for supplying liquid substance 22 into core (liquid) 21c therethrough is perforated at a portion of cladding 21a fitted on an outer surface of core (liquid) 21c. Liquid substance 22 is supplied from reservoir 23c to core (liquid) 21c by supply pump 23b by way of supply chamber 23a which surrounds the outer periphery of cladding 21a in which supply port 21e is perforated. Consequently, a surplus amount of liquid substance 22 of core (liquid) 21c is discharged from the end of cladding 21a into liquid of the object of measurement thereby to renew liquid substance 22 which forms light inputting/outputting surface 21d of the core. While supply pump 23b and supply chamber 23a are provided in the present embodiment, some other means may be used instead only if it can supply liquid substance 22 to core (liquid) 21c.

Figure 3:
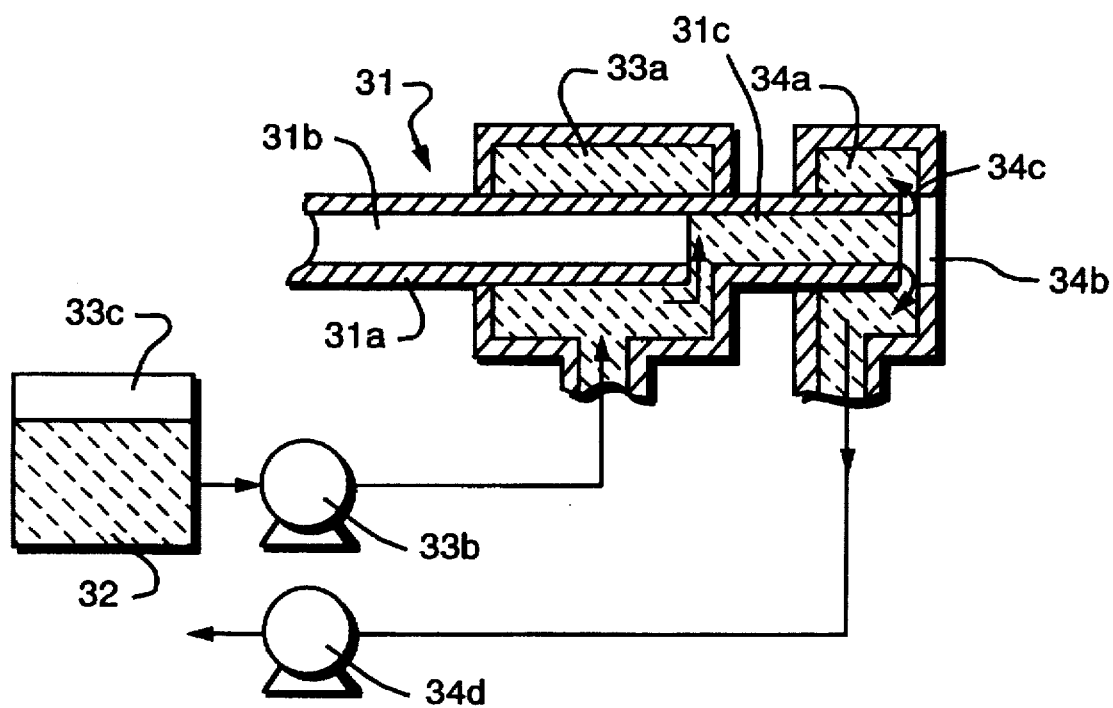
FIG. 3 is a partial liquid optical measuring of the present invention.

FIG. 3 is a partial sectional view of an intra-liquid optical measuring sensor of a third embodiment of the present invention. A recovery apparatus is formed from recovery chamber 34a and recovery pump 34d. The intra-liquid optical measuring sensor of the present embodiment is the same as that of the second embodiment except the recovery apparatus for liquid substance 32 discharged from core (liquid) 31 c.

Recovery chamber 34a for recovering surplus liquid substance 32 discharged from the end of core (liquid) 5ic is provided so as to surround the outer periphery at the end of the sensor. Recovery chamber 34a is connected to recovery pump 34d. A surface of recovery chamber 34a opposing the light inputting/outputting surface of the core is disposed with gap portion 34c left from an end of cladding 31a, and opening 34b is provided within a range within which it does not have an influence upon inputting and outputting of light to and from the core.

Where it is undesirable to discharge the liquid substance into liquid of the object of measurement, the liquid substance is recovered from the outside of the liquid of the object of measurement by the recovery apparatus.

While the recovery chamber in FIG. 3 is provided over the entire outer periphery of the end of the sensor, a recess or notch for recovery may be provided at the outer periphery of the end of the sensor while the recovery chamber is provided only around the recess or notch.

Figure 4:
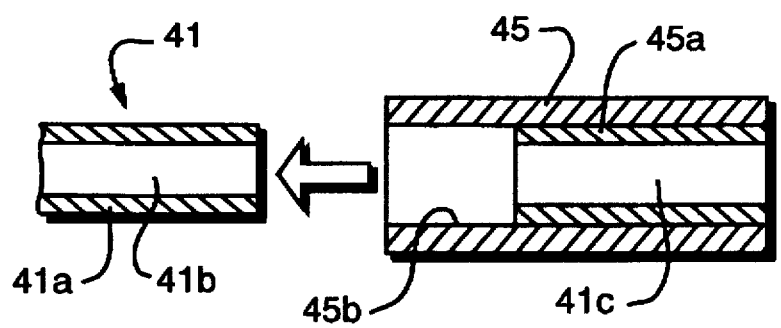
FIG. 4 is a partial sectional view of a capillary to be attached to an optical fiber of a fourth embodiment of the present invention.

FIG. 4 is a partial sectional view of a capillary attached to the end of the optical fiber of a fourth embodiment of the present invention. Capillary 45 includes cladding 45a which has an inner diameter substantially equal to the inner diameter of cladding 41a of optical fiber 41 and which is disposed along a predetermined length of an inner surface of the capillary 45. Capillary 45 is attached, at attaching portion 45b provided separately thereon, to the end of optical fiber 41 in such a manner that the inner diametrical portion of cladding 45a is contiguous through the end of core 41b.

Similar to the first embodiment, a liquid substance having a light transmitting property is filled in the inside of cladding 45a of capillary 45 and forms core (liquid) 41c. The liquid substance is held readily in the inside of cladding 45a by capillary phenomenon by surface tension with the inner surface of cladding 45a.

While, in the present embodiment, the inner diameter of cladding 45a of the capillary is substantially equal to the inner diameter of cladding 41a of the optical fiber, it may have a different inner diameter within a range within which the liquid substance in the inside of it can be held by the surface tension of the inner surface and the pressure of the liquid of the object of measurement. Where the optical fiber is formed as an aggregate of a plurality of fibers, a single capillary can be attached to the inner diameter of the capillary set equal to the inner diameter of a portion of the aggregate which corresponds to the core. Also the material of cladding 45a of the capillary may be, for example, a metal so long as the inner surface thereof is in the form of a mirrored surface which exhibits a high reflection factor to transmission light.

Further, while, in the present embodiment, cladding 45a is fitted with the inner surface of the body of capillary 45, it may alternatively be formed integrally with the body of capillary 45. Further, while the attaching portion is constructed such that the inner surface of capillary 45 is fitted with the outer surface of cladding 41a of optical fiber 41, some other attaching method may alternatively be employed.

By attaching removable capillary 45 to the end of the optical fiber, the liquid core can be provided readily in the optical measuring sensor, and also the inner diameter of the cladding can be set arbitrarily within a range within which the liquid substance in the inside of the cladding can be held by surface tension of the inner surface and pressure of the liquid of the object of measurement.

Figure 5:
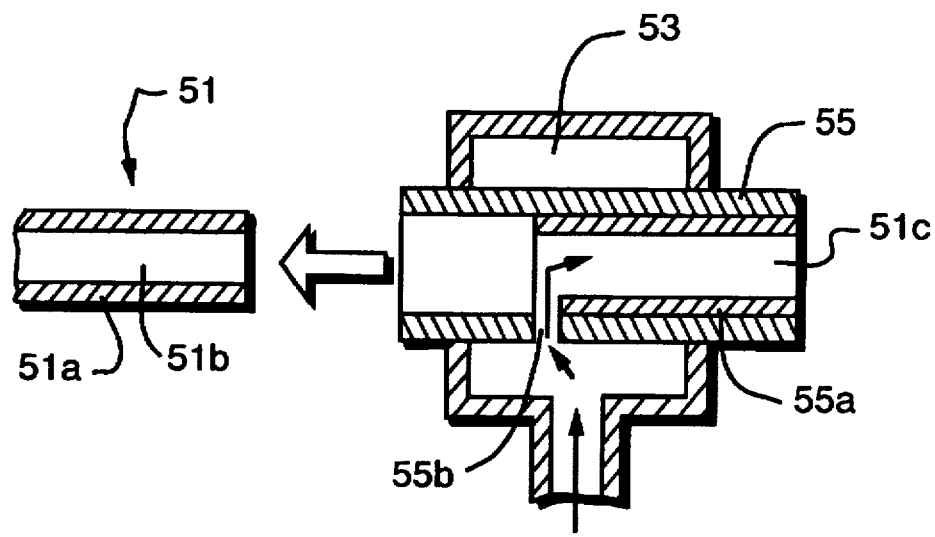
FIG. 5 is a partial sectional view of a capillary an optical fiber of a fifth sectional view of an intrasensor of a second embodiment to be attached to sensor of a first embodiment sectional view of an intrasensor of a third embodiment of the present invention.

FIG. 5 is a partial sectional view of a capillary attached to the end of the optical fiber of a fifth embodiment of the present invention. Capillary 55 has supply port 55b perforated therein through capillary 55 and cladding 55a so that the liquid substance is supplied into the inside of cladding 55a by way of supply chamber 53 which is provided around an outer periphery of cladding 55a in which supply port 55b is perforated.

The structure and the operation of the capillary are the same as in the fourth embodiment and the supplying of the liquid substance into the supply chamber and operation are the same as in the second embodiment, and accordingly, description of them is omitted here.

Figure 6:
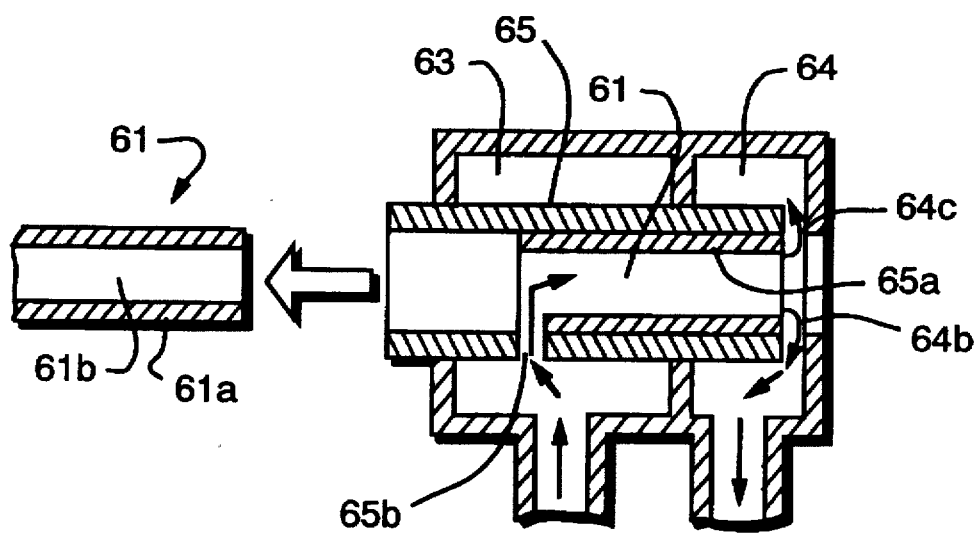
FIG. 6 is a partial sectional view of a capillary to be attached to an optical fiber of a sixth embodiment of the present invention.

FIG. 6 is a partial sectional view of a capillary attached to the end of an optical fiber of a sixth embodiment of the present invention. Capillary 65 has supply port 65b perforated therein through capillary 65 and cladding 65a so that a liquid substance is supplied into the inside of cladding 65a by way of supply chamber 63 which is provided around an outer periphery of cladding 65a in which, supply port 65b is perforated.

Recovery chamber 64 for recovering surplus liquid substance discharged from the end of the liquid core in the inside of clad 65a is provided so as to surround the outer peripheral portion of the end of the capillary. A surface of recovery chamber 64 opposing the light inputting/outputting surface of the core is disposed with gap portion 64c left from the end of cladding 65a, and opening 64b is provided within a range within which it does not have an influence on inputting and outputting of light to and from the core.

The structure and the operation of the capillary are the same as in the fourth embodiment and the supplying of liquid substance into the supply chamber and its operation are the same as in the second embodiment while the recovery of the surplus liquid substance discharged from the core and its operation are the same as in the third embodiment. Accordingly, their description is omitted here.

Figure 7A:
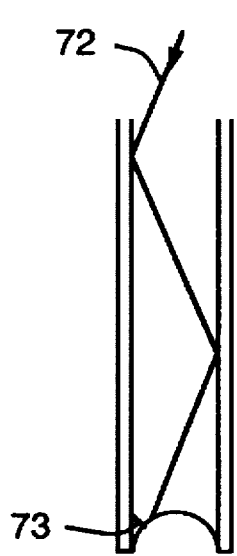
Figure 7B:
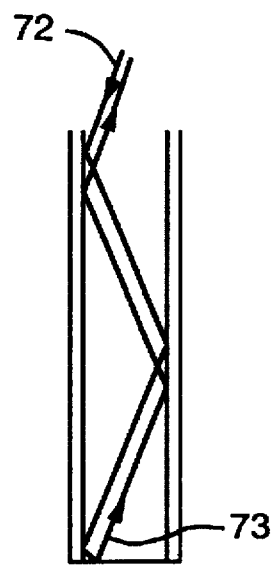
Figure 7C:
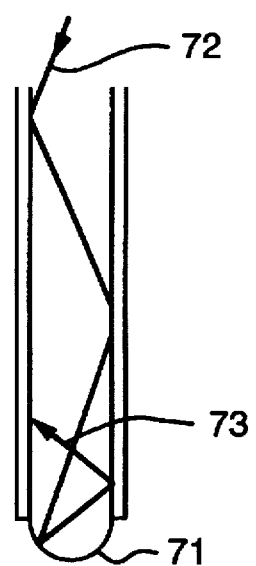

FIGS. 7(a) to 7(c) are partial sectional views showing different shapes of the light inputting/outputting surface of the liquid core of a seventh embodiment of the present invention and relationships between incident light and reflected light. In particular, FIG. 7(a) shows the end surface of the liquid core curved toward the inside of the cladding, FIG. 7(b) shows a flat end surface of the liquid core, and FIG. 7(c) shows the end surface of the liquid core curved toward the outside of the cladding.

Since the shape of the end surface of the light inputting/outputting surface of the liquid core has an influence on the outputting/inputting efficiency of probe light and hence upon the detection sensitivity, it is desirable to control the shape to some degree.

Since the relationship between input light and reflected light varies depending upon the shape of the end surface as seen from FIGS. 7(a) to 7(c), if, though not shown, the amount of reflected light is monitored on the measuring instrument side of the optical fiber and the amount of the liquid substance to be supplied to the liquid cure is adjusted by a control apparatus in accordance with the result of the monitoring, then the desired shape of the light inputting/outputting face of the liquid core can be determined.

The liquid substance to be used to form the liquid core preferably satisfies such conditions as being high in water repellency and low in surface energy, not having an absorptivity of light in the visible ray and ultraviolet ray regions, being superior in chemical stability and being adapted so that a product of a desired viscosity can be obtained. It is considered that silicone oil is an optimum substance which satisfies the conditions described above.

Further, by rising, for the liquid core, a solvent which has a high affinity with the substance which forms the object of measurement, collection and detection with a high degree of efficiency can be achieved. Accordingly, the silicone oil mentioned above can be used for high sensitivity detection of an intra-liquid minor component having a lipophilic property.

Since maritime organisms cannot live in fresh water, where the intra-liquid optical measuring sensor is used in sea water, contamination by maritime organisms can be reduced by using fresh water as the liquid substance.

Deposition of organisms onto an intra-liquid optical measuring sensor occurs with a structure in liquid which has a certain hardness. According to the method of the first embodiment described above, since the object of deposition of maritime organisms is in the form of liquid, deposition of organisms is suppressed due to the effects of the smoothness of the surface, the fluidity and so forth compared with the conventional methods which employ a solid core.

Further, even if deposition occurs, due to the increase in weight as the deposit grows, the deposit is exfoliated and removed together with part of the liquid.

Where a liquid substance having a high water repellency and a high hydrophobic property such as silicone oil is used, the amount of organisms which may be deposited is further reduced due to deterioration of the breeding environment.

Where the intra-liquid optical measuring sensor is used in sea water, contamination by maritime orgasms can be reduced at reduced cost by using fresh water as the liquid substance.

Where a capillary provided with a liquid core portion, as in the fourth embodiment is used, the liquid core can be provided readily in the optical measuring sensor. Besides, the inner diameter of the cladding can be set to an arbitrary inner diameter only if it is within a range within which the liquid substance in the inside can be held by surface tension of the inner face and pressure of liquid of the object of measurement. For example, where the optical fiber is formed as an aggregate of a plurality of fibers, a single capillary can be attached with the inner diameter thereof set, equal to the inner diameter of a portion of the aggregate which corresponds to the core.

Also for the material of cladding 45a of the capillary, a metal of low cost can be used if the inner surface of it has a mirrored surface which exhibits a high reflection factor to transmission light.

Further, in the method wherein the liquid substance is supplied to the liquid core from the outside as in the second and fifth embodiments, since the liquid substance which contacts with liquid of the object of measurement is renewed together with the contaminant substances, organisms or contaminant substances deposited onto the light inputting/outputting face and contaminated portions originating from such organisms or contaminant substances can be removed with certainty.

Where a recovery apparatus for surplus liquid substance discharged from the liquid core is provided as in the third and sixth embodiments, scattering of overflowing liquid substance and contaminant substances into liquid of the object of measurement can be prevented.

Further, by providing a monitor for measuring the amount of reflected light produced at the end surface of the core of the liquid substance and a control apparatus for controlling the amount of the liquid substance to be supplied in accordance with the result of the measurement of the monitor, the shape of the end surface of the core of the intra-liquid optical measuring instrument can be controlled so as to have a desired shape by which a high outputting/inputting efficiency of probe light and hence a high detection sensitivity can be obtained.

The variation of the optical transmission function caused by the liquid substance core very small since its transmission distance is very short, and is fixed due to the transmission distance. Accordingly, by evaluating the influence of the variation in advance, measurement with a high degree of reliability can be achieved in a condition wherein the liquid substance core always exists.

Further, according to the present invention, since it is not necessary to jet a large amount of fresh water to or to cause a large amount of fresh water to stay around the sensor portion as in the prior art, the environment in the region of the object of measurement does not vary, and consequently, continuous measurement with a high degree of reliability can be performed simply and readily.

By using such a method as described above, it is possible to suppress deposition of organisms or foreign articles, which inevitably presents an obstacle to measurement making use of an optical fiber which is performed in the water, and continuous measurement for a long time can be achieved free from maintenance.

It is to be understood, however, that although the characteristics and advantages of the present invention have been set forth in the foregoing description, the disclosure is illustrative only, and changes may be made in the arrangement of the parts within the scope of the appended claims.

What is claimed is:

1. An intra-liquid optical measuring sensor adapted for measuring a property of a liquid, said sensor comprising an optical fiber having a core and a cladding, said core including a liquid portion for directly contacting said liquid, said liquid portion being composed of a liquid substance having a light transmitting property and communicating with the liquid whose property is to be measured by said sensor.

2. An intra-liquid optical measuring sensor as claimed in claim 1, further comprising a supply apparatus for supplying the liquid substance to the liquid portion of said core.

3. An intra-liquid optical measuring sensor as claimed in claim 2, further comprising a recovery apparatus for recovering a portion of said liquid substance which flows out from said optical fiber.

4. An intra-liquid optical measuring sensor adapted for measuring a property of a liquid, said sensor comprising an optical fiber having a core and a cladding, said sensor also comprising a capillary pipe having a liquid substance inside an inner diameter portion of said pipe, said inner diameter portion having a diameter that is at least equal to an outer diameter of said core and within a range within which said liquid substance can be held by surface tension of an inner surface of said pipe and pressure of said liquid whose property is to be measured by said sensor, said liquid substance having a light transmitting property, said pipe being attached to an end of said optical fiber such that the inner diameter portion of said pipe is disposed continuously to said end of said fiber so as to form a liquid core containing said liquid substance, said liquid core being in communication with said liquid whose property is to be measured by said sensor.

5. An intra-liquid optical measuring sensor as claimed in claim 4, further comprising a supply apparatus for supplying the liquid substance to the inner diameter portion in said capillary pipe.

6. An intra-liquid optical measuring sensor as claimed in claim 5, further comprising a recovery apparatus for recovering a portion of said liquid substance which flows out from said capillary pipe.

7. An intra-liquid optical measuring sensor as claimed in claim 2, further comprising a monitor for measuring an amount of reflected light produced at an end surface of said liquid portion of said core, said end surface being in contact with said liquid whose optical property is to be measured by said sensor, and a control apparatus for controlling amount of said liquid substance to be supplied to the liquid portion based upon measurement of said monitor so as to maintain shape of said end surface.

8. An intra-liquid optical measuring sensor as claimed in claim 1, wherein silicone oil is said liquid substance.

9. An intra-liquid optical measuring sensor as claimed in claim 1, wherein water is said liquid substance.

10. A contamination preventing method for an intra-liquid optical measuring sensor adapted for measuring a property of a liquid, said sensor including an optical fiber, said method comprising:

providing a core of said optical fiber with a liquid portion composed of a liquid substance; and directly contacting a contacting portion of said liquid portion with said liquid whose property is to be measured by said sensor, said liquid substance in said liquid portion being in communication with said liquid whose property is to be measured by said sensor and acting to reduce deposition onto said contacting portion of contaminant substances from said liquid whose property is to be measured.

11. A contamination preventing method for an intra-liquid optical measuring sensor as claimed in claim 10, wherein said liquid substance is supplemented from the outside so as to replenish the liquid substance at the contacting portion of said core.

12. An intra-liquid optical measuring sensor as claimed in claim 5 further comprising a monitor for measuring an amount of reflected light produced at an end surface of said liquid portion of said core, said end surface being in contact with said liquid whose property is to be measured by said sensor, and a control apparatus for controlling amount of said liquid substance to be supplied to the liquid portion based upon measurement of said monitor so as to maintain shape of said end surface.

13. An intra-liquid optical measuring sensor as claimed in claim 4, wherein silicone oil is said liquid substance.

14. An intra-liquid optical measuring sensor as claimed in claim 4, wherein water is said liquid substance.

* * * * *